US009717852B2

(12) United States Patent
Einwachter (10) Patent No.: US 9,717,852 B2
(45) Date of Patent: Aug. 1, 2017

(54) CARTRIDGE HOLDER AND PEN-TYPE INJECTOR

(71) Applicant: SANOFI-AVENTIS DEUTSCHLAND GMBH, Frankfurt am Main (DE)

(72) Inventor: Robin Einwachter, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/391,055

(22) PCT Filed: Apr. 8, 2013

(86) PCT No.: PCT/EP2013/057270
§ 371 (c)(1),
(2) Date: Oct. 7, 2014

(87) PCT Pub. No.: WO2013/153011
PCT Pub. Date: Oct. 17, 2013

(65) Prior Publication Data
US 2015/0073350 A1 Mar. 12, 2015

Related U.S. Application Data

(60) Provisional application No. 61/665,421, filed on Jun. 28, 2012.

(30) Foreign Application Priority Data

Apr. 11, 2012 (EP) .................................... 12163800

(51) Int. Cl.
*A61M 5/28* (2006.01)
*A61M 5/24* (2006.01)

(52) U.S. Cl.
CPC ................ *A61M 5/28* (2013.01); *A61M 5/24* (2013.01); *A61M 2005/2407* (2013.01); *A61M 2005/2492* (2013.01)

(58) Field of Classification Search
CPC .. A61M 5/24; A61M 5/28; A61M 2005/2403; A61M 2005/2407;
(Continued)

(56) References Cited

U.S. PATENT DOCUMENTS

| 533,575 A | 2/1895 | Wilkens |
| 5,030,209 A * | 7/1991 | Wanderer ............. A61B 5/1444 604/198 |

(Continued)

FOREIGN PATENT DOCUMENTS

| CN | 101557850 A | 10/2009 |
| EP | 0937471 A2 | 8/1999 |

(Continued)

OTHER PUBLICATIONS

International Search Report for Int. App. No. PCT/EP2013/057270, completed Jun. 25, 2013.

*Primary Examiner* — Bradley Osinski
(74) *Attorney, Agent, or Firm* — McDonnell Boehnen Hulbert & Berghoff LLP (57) ABSTRACT

A cartridge holder for a drug delivery device is presented having snap fastening connection means to fasten the cartridge holder to a housing of the drug delivery device, wherein the fastening connection means are provided with at least on basically rectangular window for receiving a locking element of said housing. The invention is further directed to a pen-type injector equipped with a respective snap fastening connection for the cartridge holder.

8 Claims, 8 Drawing Sheets

(58) Field of Classification Search
CPC .. A61M 2005/2411; A61M 2005/2414; A61M 2005/2433; A61M 2005/2437; A61M 2005/2485; A61M 2005/2492
USPC ....... 604/187, 192, 200, 201, 218, 232, 233, 604/234, 235
See application file for complete search history.

(56) References Cited

U.S. PATENT DOCUMENTS

| | | |
|---|---|---|
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 2001/0034507 A1 | 10/2001 | Kirchhofer et al. |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2009/0275916 A1 | 11/2009 | Harms et al. |
| 2010/0042054 A1* | 2/2010 | Elahi et al. .................. 604/211 |
| 2012/0053528 A1* | 3/2012 | Bollenbach et al. ......... 604/192 |

FOREIGN PATENT DOCUMENTS

| | | |
|---|---|---|
| EP | 0937476 A2 | 8/1999 |
| EP | 1944050 A2 | 7/2008 |
| EP | 1974761 A2 | 10/2008 |
| EP | 1855743 | 12/2008 |
| WO | 99/16487 | 4/1999 |
| WO | 99/38554 A1 | 8/1999 |
| WO | 01/10484 A1 | 2/2001 |
| WO | 2008/059063 A1 | 5/2008 |
| WO | 2011/051366 | 5/2011 |

* cited by examiner

Table 1

FIG. 6

Table 2

FIG. 7

Table 3

FIG. 8

Table 4

FIG. 9

Table 5

FIG. 10

Table 6

FIG. 11

Table 7

FIG. 12

Table 8

FIG. 13

Table 9

CARTRIDGE HOLDER AND PEN-TYPE INJECTOR

CROSS REFERENCE TO RELATED APPLICATIONS

The present application is a U.S. National Phase Application pursuant to 35 U.S.C. §371 of International Application No. PCT/EP2013/057270 filed Apr. 8, 2013, which claims priority to European Patent Application No. 12163800.1 filed Apr. 11, 2012 and U.S. Provisional Patent Application No. 61/665,421, filed Jun. 28, 2012. The entire disclosure contents of these applications are herewith incorporated by reference into the present application.

TECHNICAL FIELD

The present invention is directed to a cartridge holder for a drug delivery device with snap fastening connection means to fasten the cartridge holder to a housing of the drug delivery device, wherein the fastening connection means are provided with at least one basically rectangular window for receiving a locking element of said housing. The invention further refers to a pen-type injector equipped with a respective snap fastening connection for the cartridge holder.

BACKGROUND

Such injectors are regularly used by persons who do not have formal medical training. Accordingly, the application comes along with circumstances that set a number of requirements for drug delivery devices of this kind. In case of improper use such as unauthorized disassembly actions there is the risk of contamination of the medicament stored in the cartridge. Also mechanical parts of the device could be damaged. Therefore, the device must be robust in construction in order to prevent fatal manipulation of the components. Especially with regard to the cartridge holder, which is connected to the housing of the drug delivery device, there is demand for a reliable connection easy to manufacture and to assemble but also safe regarding to any kind of manipulation.

US 2001/0034507 A1 discloses a cartridge holder in which a cartridge is accommodated, the cartridge holder being mechanically coupled to a sleeve-shaped mechanism holder by means of a bayonet lock. The cartridge holder shown in EP 1 855 743 B1 is provided with snap fastening connection means to couple a sleeve-like cartridge holder to a housing. The fastening connection means include a pair of apertures provided in the wall of the sleeve-like cartridge holder at a section facing the housing of the drug delivery device and for receiving a locking element of the housing. The apertures are formed as rectangular windows continuously reaching through the cartridge holder. However, rectangular windows generally have walls intersecting at an angle of 90°, which means they have acute-angled edges, respectively corners. In case of improper use or unauthorized disassembly efforts, e.g. by trying to pull or lever out the cartridge holder from the housing, mechanical pressures in the material, especially in the connection means area arise. As a result of the sharp edges and corners of the windows, notch effects occur that cause local stress concentrations in the corner area. Often, plastic materials are used for producing drug delivery devices. Especially at low temperatures, materials of this kind can tend to become brittle. In this case, the concentrated stress distribution in the corner area may result in tear or breakage of the window geometry and the material surrounding the window.

SUMMARY

It is an object of the present invention to conceive a suitable solution in terms of stress resistance, especially at low temperature conditions. This is obtained by a cartridge holder as defined in claim 1 and a drug delivery device as defined in claim 9.

The present invention is based on the idea that each of the corners of the window is provided with a round contour. The round contour can come along with a curved shape of the intersection of two adjacent walls. Preferably, the round contour is designed as a clearance or recess in the material surrounding or being adjacent to the respective corners. In this respect it is not necessary that the whole clearance or recess is rounded, e.g. a circular clearance. Moreover, the clearance or recess may comprise at least one straight or rectangular section and at least one rounded section, e.g. a segment of a circle, ellipse or oval. Further, it is preferred to provide the rounded corners such that the rectangular opening area of the window is not affected or reduced, i.e. the rounded corners do not interfere in the region in which the snap protrusions (locking elements) of the housing engage.

The mechanical forces the connection means between cartridge holder and drug delivery device are subjected to and the flux of force in the area of the corners of the window is redirected more smoothly. Due to the geometry, notch effects are minimized. Especially at low temperatures, the geometry reduces critical stress peaks in the corner area as local stress is distributed over a greater range. The connection means benefit from a significant less breakage tendency and higher breakage strength. In the field of drug delivery devices, materials such as Bormed RF825MO have proved to be effective. In regard of the specifications emerging from the patient's use and material properties, all requirements concerning mechanical and thermal load capacities can be met by the specific window design.

According to a first embodiment of the present invention, the round contour may be formed into at least one of the corners of the window in a notch-like manner. The curved corner may for example be set back a distance with respect to the adjacent side walls of the window, respectively the basic rectangular shape of the window. A suitable locking element such as a bayonet locking element or a radially projecting tab-like element may preferably have a basically rectangular shape, too. A direct application of force into the corner area is avoided because the locking element is substantially supported by the side walls of the window and does not contact the corner area.

Preferably, the rounded notch extends in a circumferential direction and/or axial direction with respect to a longitudinal axis of the cartridge holder. The stress forces in the material are distributed over a large area thus reducing local stress peaks to a minimum.

Preferably, in each of the corners on one side of the basically rectangular window in a circumferential direction first notches are provided that extend in circumferential direction and in each of the corners on the opposite side of the window second notches are provided that extend in axial direction. The second notches can be provided such that one of the second notches extends towards a distal end of the device where a needle arrangement can be attached while the other of the second notches extends towards a proximal end of the device having actuating or comparable means to induce a force for discharging a medicament from the cartridge.

In another preferred embodiment of the invention, at least a portion of each of the first notches is formed as an extension of respectively one of two opposite sides of the window. Further, at least a portion of each of the second notches is formed as an extension of a third side of the window. By this arrangement, stress concentrations and local stress peaks are kept away from the corners in a very efficient way. Further, the extensions provide a large contact surface for the locking element received in the window. Forces transmitted through the locking element are mainly supported by the sides of the window while keeping the stress forces away from the corners.

In order to maintain a fixed position of the locking element in the window and to prevent unintended relative movement between locking element and window, e.g. due to manufacturing tolerances, the first notches may be arranged in such way that an intermediate section between the first notches constitutes a lug which is preferably resilient and which is adapted to exert a force toward the locking element. This embodiment also meets the requirements concerning an easy and convenient assembly. The basic dimensions of the window can be wider than the dimensions of the locking element thereby enabling an easy snapping action without any jamming effects. The lug is adapted to bias the locking element toward the side wall opposite to the lug. A reliable locking with a tight fit combined with a simple attachment of the cartridge holder to the housing is thus achieved. The lug can be arranged on either side of the window, exerting a force in proximal, distal or any other direction.

An absolutely firm seat of the locking element in the window can be achieved by adapting the dimensions of the basically rectangular shape of the window to receive the locking element which is associated with the housing in a tight manner. Even when high forces are applied to the connection between cartridge holder and housing, relative movement between those two elements is prevented by what impact loads and stresses in the connection are eliminated.

Preferably, according to a further embodiment of the invention, on at least a portion of the outer surface of the cartridge holder at least one axially elongated spline element, preferably integrally formed with a cartridge holder, is disposed which is adapted to engage a corresponding groove associated with or formed into the housing. For example, a multiplicity of parallel ribs that extend in the longitudinal direction of the cartridge holder can be spaced at regular or irregular intervals over the outer circumference of the cartridge holder. The ribs act as guidance means and facilitate the insertion of the cartridge holder into the housing. Further, they prevent relative rotational movement between the cartridge holder and the housing. In a further improvement of the invention, a plurality of spline elements is provided around the periphery of the cartridge holder distributed in such manner, that the cartridge holder can only be fastened to the drug delivery device when the cartridge holder and the drug delivery device are in a predetermined relative rotational position to each other. For this purpose, the plurality of spline elements is preferably distributed around the periphery of at least a section of the cartridge holder in a non rotationally symmetric manner. In this context, the arrangement of the spline element on the cartridge holder can serve as coding. The cartridge holder can only be connected to a housing with spline grooves, said spline grooves being arranged in a corresponding distribution which means both of the parts are encoded and the coding of each of the elements is compatible to the other. In regard of manufacturing issues, this feature ensures that only the dedicated cartridge holder is attached to the drug delivery device and that drug delivery device and cartridge holder are in the correct relative position to each other.

The object of the present invention is further achieved by a pen-type injector, having a housing and a cartridge holder for a cartridge containing a medical product such as a medicament, wherein the housing and the cartridge holder are held together by a snap fastening connection as described above. In particular, the advantages of the present invention make a positive difference when the pen-type injector is a disposable injection device. Such devices can be thrown away or recycled after the content of the medicament has been exhausted. Preferably, the snap fastening connection is designed such that the housing of the pen-type injector and the cartridge holder cannot be separated without causing damage and/or destroying same. The pen-type injector may be designed similar to that known from EP 1 603 610.

Tables 1 to 9 as illustrated in FIGS. 5-13 show in exemplary form the improved strength capacity and stress resistance of a drug delivery device that is provided with the connection means of invention, the window of the cartridge holder being referred to as clip window. The enhanced absorption of impact stresses acting on the drug delivery device at different locations, varied temperature conditions and under different preload condition is displayed in comparison to comparative examples that relate to drug delivery devices provided with regular connection means.

Tables 1 to 4 present impact test results at very low temperature conditions (2° Celsius) under different preload conditions with the impact forces applied directly onto the clip window (tables 1 and 2), respectively between clip windows (tables 3 and 4). In each series of testing, the new window design shows an improved absorbance of short-time stress peaks, while as to state-of-the-art designed windows a higher breakage tendency is indicated at the same time.

But not only at low temperature condition, where plastic materials are regularly more susceptible to breakage effect, also under normal, respectively room temperature conditions, drug delivery devices significantly benefit from the inventive window design. Especially when impact forces directly act onto the window, stress absorption is more efficient (tables 5 to 8). Hence, under all conditions, the present invention offers a reliable and resistant connection between cartridge holder and the injector.

Figure 13:
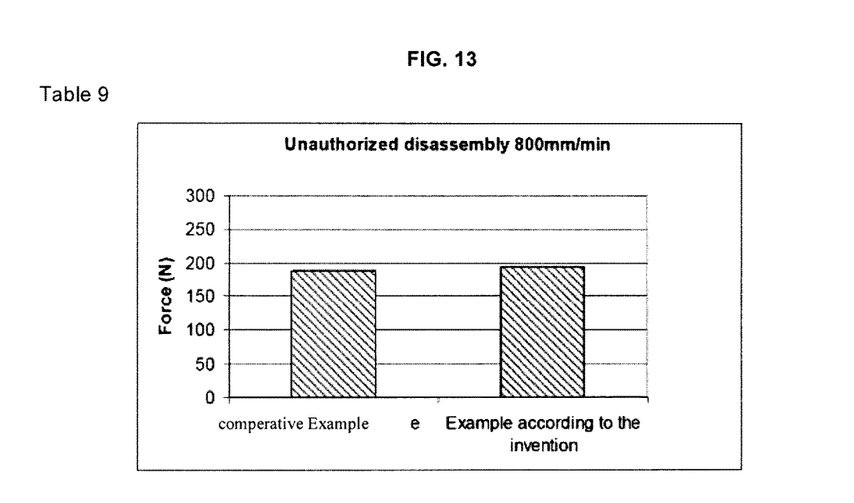
FIG. 13 shows Table 9 listing testing series representing an unauthorized disassembly action.

As to the influence of the inventive connection means on manipulation safety, table 9 displays the result of a testing series representing an unauthorized disassembly action with 800 mm/min disassembly movement. Compared to state-of-the-art designs, the new window design results in significantly higher forces necessary to successfully manipulate the connection. Thus, under all conditions and manipulation actions, the connection means of the invention ensure a high degree of safety for a drug delivery device regarding to any kind of manipulation.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

In the following, the invention will be described by a way of an example and with reference to the schematic drawings in which.

DETAILED DESCRIPTION

Figure 1:
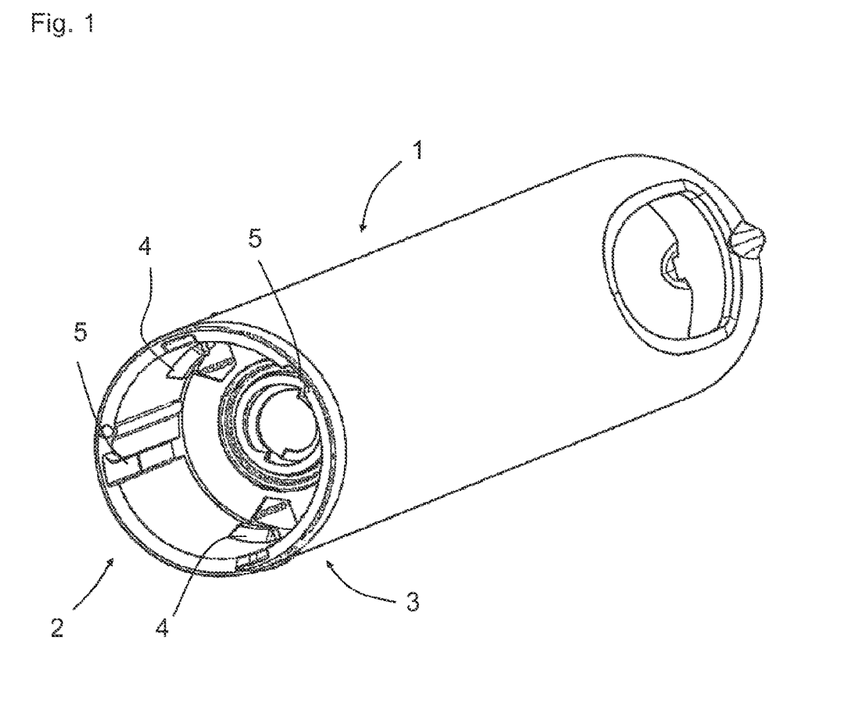
FIG. 1 shows a perspective view of a housing of a drug delivery device.

FIG. 1 shows a housing 1 of a drug delivery device for receiving a cartridge holder (FIG. 2) containing a medicinal product for example a medicament such as insulin. The housing 1 is of sleeve-like shape. At the distal end 2 of the housing 1 a section 3 is formed as an opening to receive a cartridge holder and to be locked therewith. On the inner surface of the receiving section 3 of the housing 1, a set of locking elements 4 is disposed projecting radially inwardly from the inner surface of the inner wall of the housing 1 and being basically of rectangular shape with a tapered or chamfered edge facing towards the distal end and the cartridge holder. In the inner wall, there is also formed a set of spline grooves 5 extending in longitudinal direction from the distal end 2 of the housing 1 in the opposite direction toward a proximal end.

The spline grooves 5 are arranged such as to establish a keyed connection with corresponding spline elements on the cartridge holder. The same applies to the locking elements 4 that are adapted to be received in respective receptacles in the cartridge holder.

Figure 2:
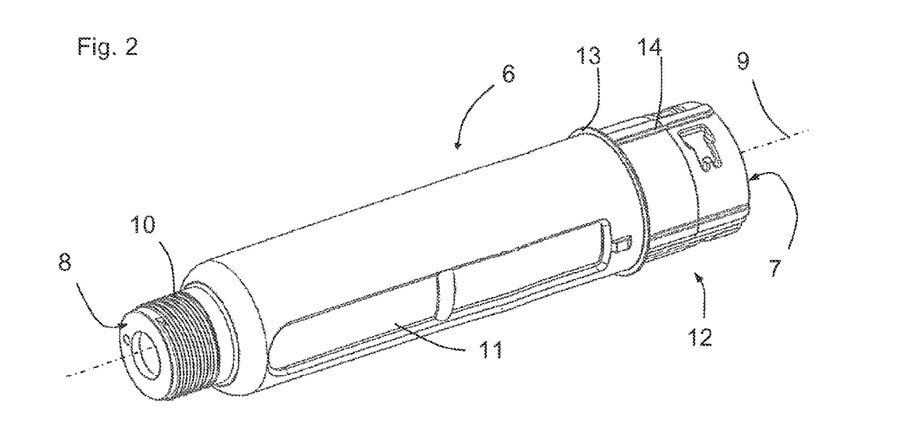
FIG. 2 shows a perspective view of a cartridge holder in accordance with a first embodiment of the present invention.

FIG. 2 shows the cartridge holder 6 adapted to be connected with the housing 1 shown in FIG. 1. The cartridge holder 6 has a proximal end 7 and a distal end 8. The proximal end 7 is adapted to be connected to the receiving section 3 of the housing 1 shown in FIG. 1. The cartridge holder 6 has an elongated tube-like shape, i.e. it is substantially designed as a cylindrical body for receiving a cartridge or an ampoule (not shown) and having a longitudinal axis 9. At the distal end 8 of the cartridge holder 6, there is a section onto which a needle arrangement can be mounted. For this purpose, the section is provided with a helical thread 10 arranged on the outside of the distal end section 8. Other suitable attachment means could be used instead of or in addition to a thread.

Figure 3:
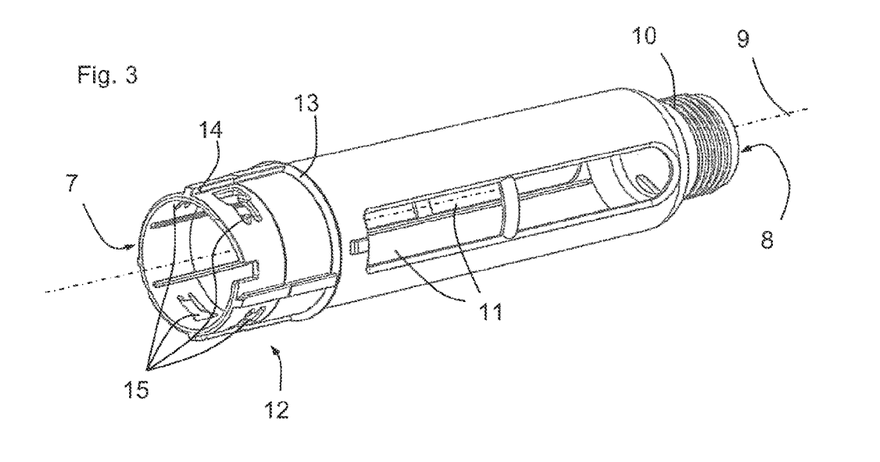
FIG. 3 shows a perspective view of the cartridge holder shown in FIG. 2 from the opposite direction.

On a substantially cylindrical section of the cartridge holder 6, a continuous opening 11 extending an axial direction is formed into the cartridge holder. A similar opening is provided on the radially opposite side of the cartridge holder 6, which can be best seen in FIG. 3. The cartridge can be inserted into the cartridge holder 6 through its proximal end. For the patient's convenience and in regard to safety requirements, the filling level of the cartridge and other important information can be visually checked through the opening 11. In addition or as an alternative to the openings 11, the cartridge holder 6 may be made at least partly of a transparent or translucent material.

The cartridge holder 6 and the housing 1 can be connected by snap fastening connection means that fasten the cartridge holder 6 to the housing 1. For this purpose, on its proximal end 7, the cartridge holder 6 is provided with an insertion section 12. The insertion section 12 is separated from the cylindrical section with the openings 11 by a collar 13, the collar being formed on the outer circumference of the holder 6 and extending radially outwardly. The collar 13 is adapted to abut the distal end of housing 1 when the insertion section is inserted into the receiving section 3 of housing 1.

On the outer surface of the insertion section 12, four longitudinal spline elements or ribs 14 extending in axial direction from the proximal end 7 toward the collar 13 are disposed. The longitudinal ribs 14 are adapted to engage the spline grooves 5 formed in the receiving section 3 of housing 1 to establish a keyed connection in radial direction to prevent relative rotational movements between the housing 1 and the cartridge holder 6 but to allow relative axial movement e.g. for the assembly process. The insertion section 12 also has a number of irregularly spaced windows 15 close to the proximal end 7. As the opening 11, the windows 15 are continuous openings through which the inner section of the cartridge holder 6 can communicate with the outside.

Figure 4:
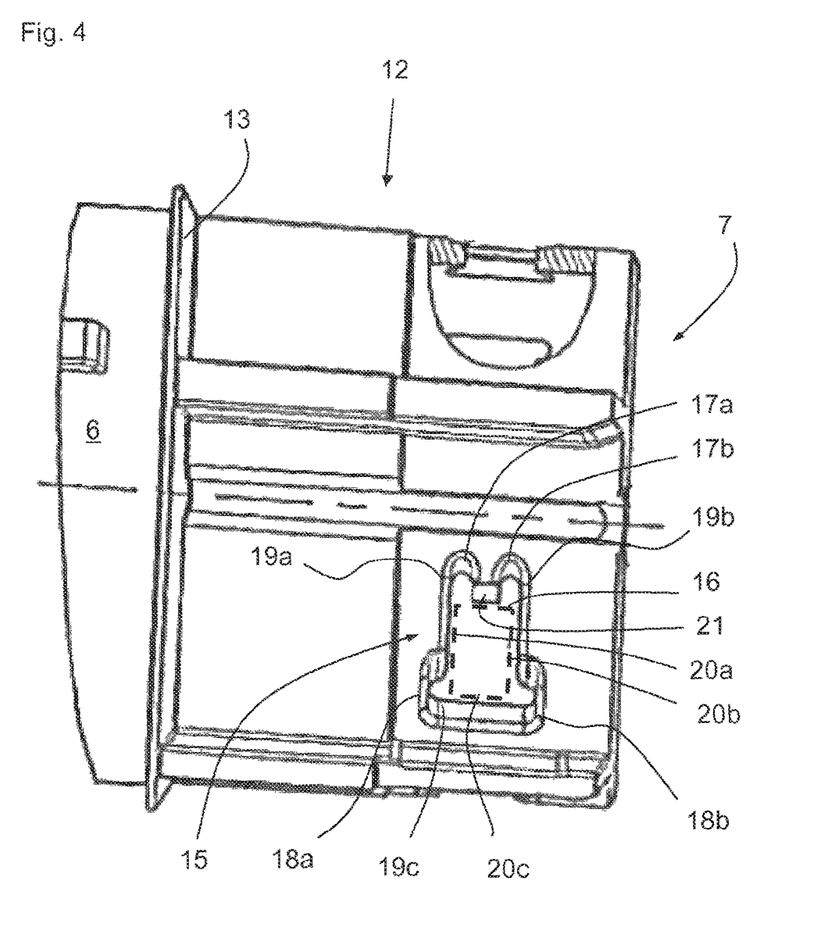
FIG. 4 shows a side view of the connection section of the cartridge holder shown in FIGS. 2 and 3.
Figure 5:
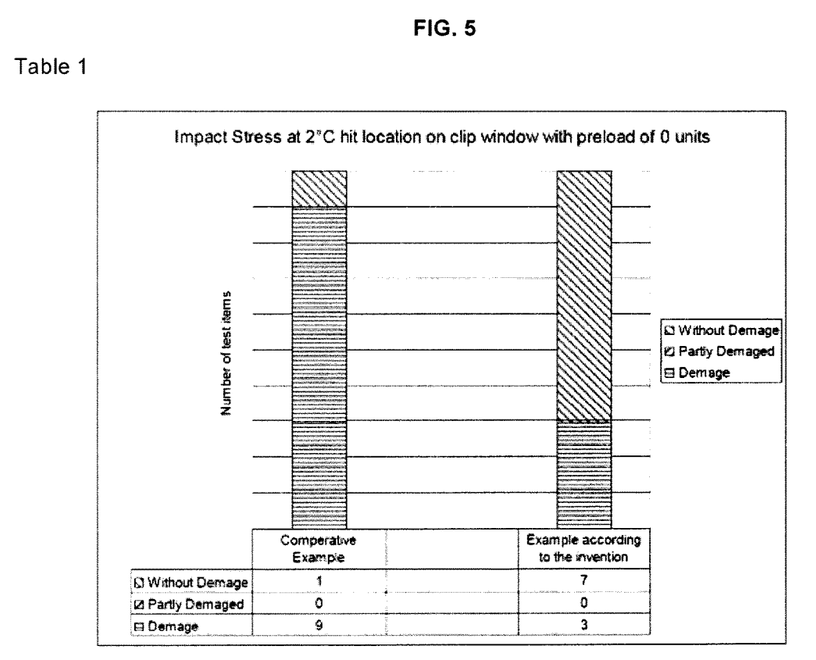
FIGS. 5-12 shows Tables 1-8 listing impact test results.
Figure 6:
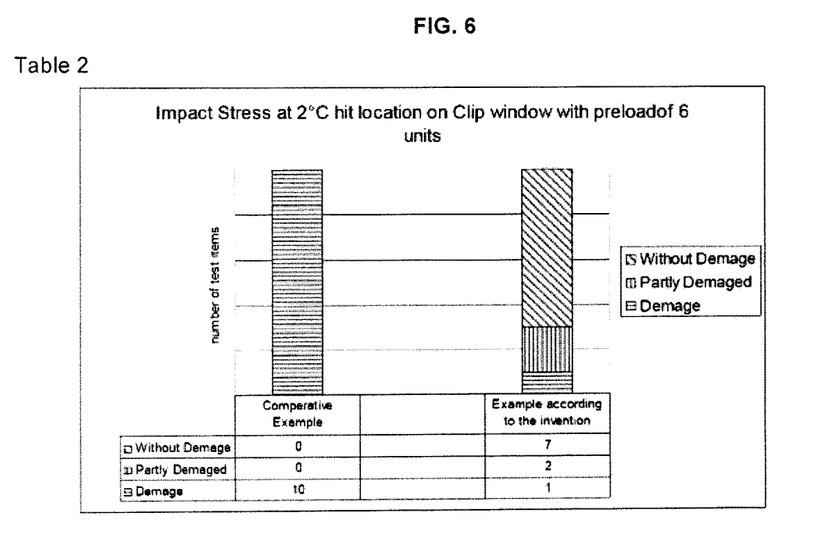
Figure 7:
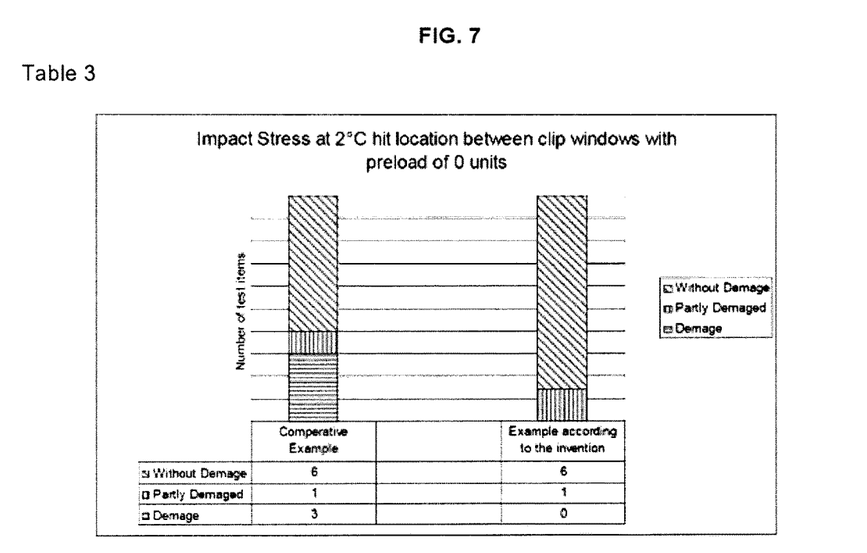
Figure 8:
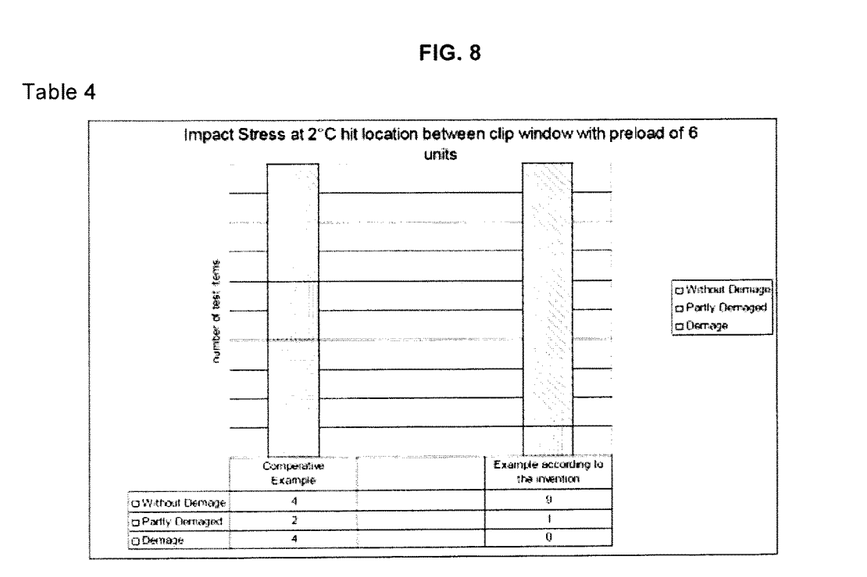
Figure 9:
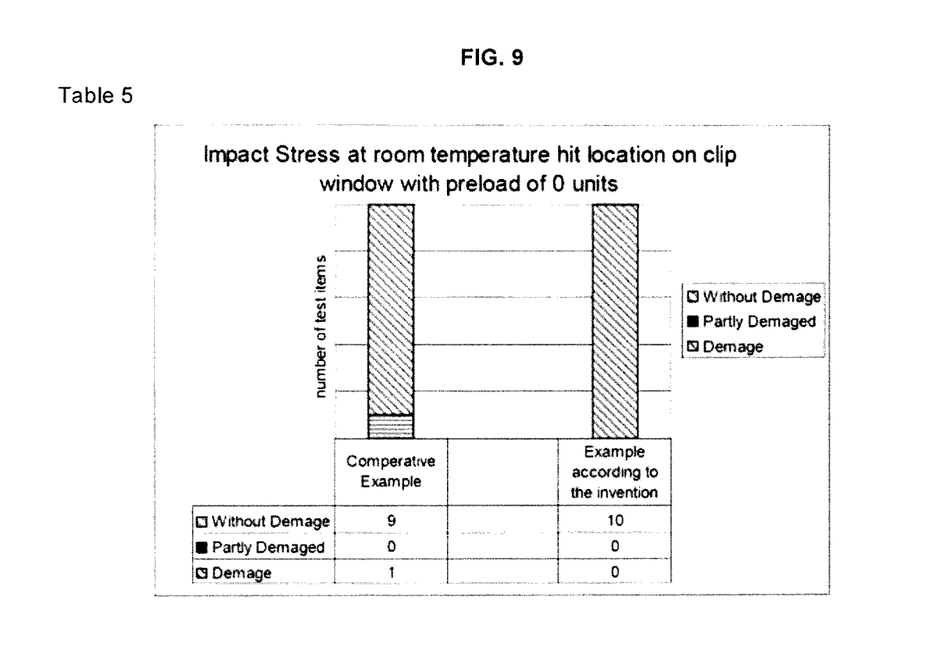
Figure 10:
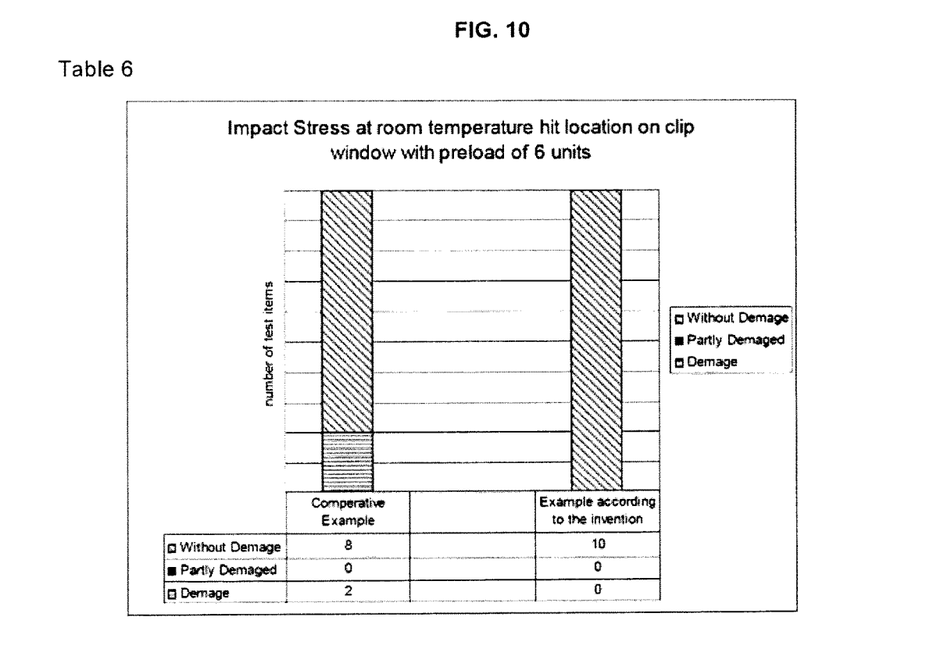
Figure 11:
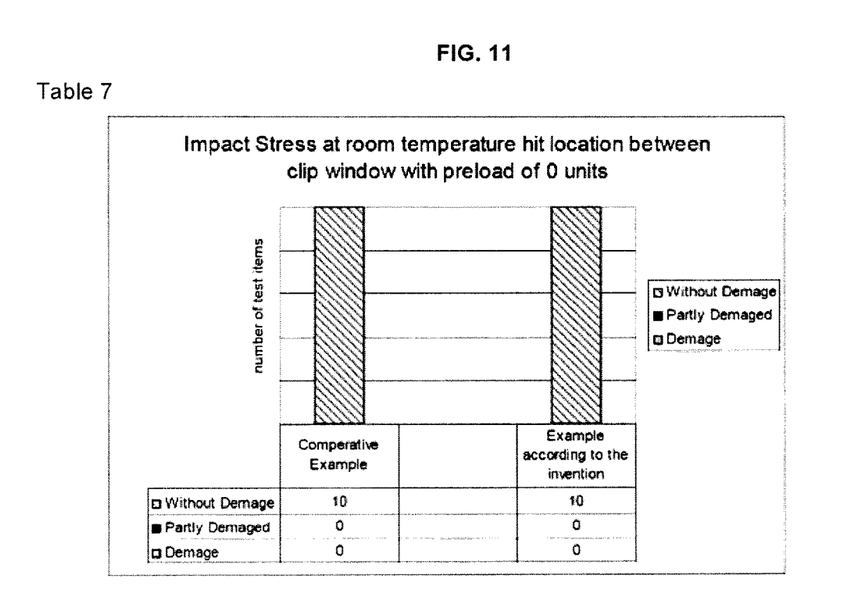
Figure 12:
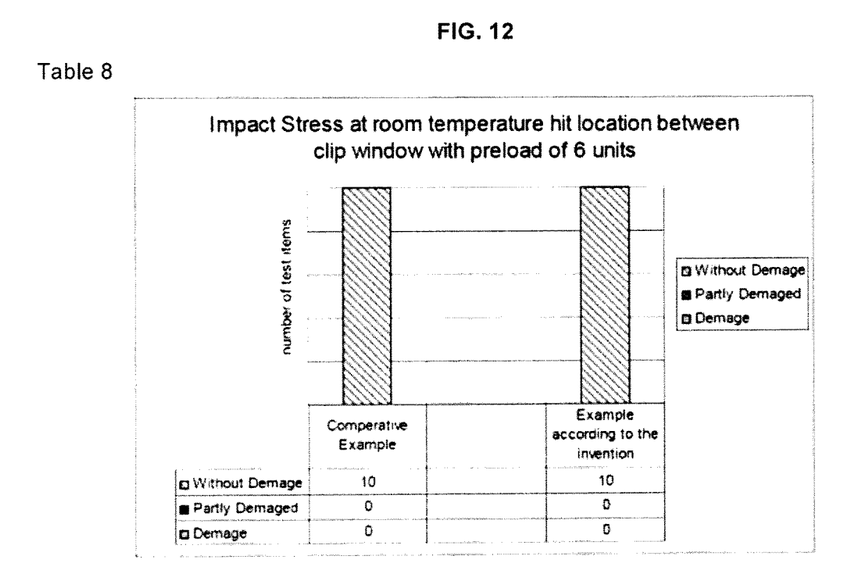

An enlargement of section 12 is shown in a side view in FIG. 4 revealing the specific geometry of the windows 15. The window 15 is basically of a rectangular shape as indicated by a broken line 16. The basic shape of the window 15 conforms in its dimensions to the locking elements 4 which means that the locking elements 4 that are basically of an rectangular shape as well conform to the size of the rectangular shape in their dimensions. Given the basic rectangular shape 16 of the window 15 FIG. 4 shows that each of the four corners of the window 15 is provided with a round contour diverting from the basic rectangular shape 16 of the window 15.

The round contour is formed into the corners in a notch-like manner, which means the round contour of the edge is set back a distance from respective edge of the basic rectangle. Accordingly, on one side of the window 15 in circumferential direction, there are first notches 17a, 17b formed into the window 15. Opposite the first notches 17a, 17b, there are second notches 18a, 18b formed into the window 15. A distal section of the first notch 17a is an extension 19a of a distal side 20a of the rectangle 16 of the window 15. One proximal section of the first notch 17b is an extension 19b of an opposite proximal side 20b of the rectangle 16 of the window 15. One section of each of the second notches 18a, 18b is formed as an extension 19c of a third side 20c of the window 15.

The first notches 17a, 17b are substantially arranged in a parallel relationship so as to form an intermediate section in-between said section constituting a resilient lug 21.

In order to connect and to fasten the cartridge holder 6 to the housing 1, the cartridge holder 6 is inserted with its insertion section 12 into the receiving section 3 of the housing 1. The longitudinal splines 14 engage with the spline grooves 5 of the receiving section 3 and the locking elements 4 are received in the window 15. In the window 15, the lug 21 exerts a force toward the locking element 4 with the tendency to bias the locking element 4 toward the third side 20c of the window 15 thereby securing a firm seat of the locking element 4 in the window 15. In case, an inexperienced user now tries to pull the cartridge holder 6 out of the housing 1 or accidentally buckles the cartridge holder relative to the housing 1, the connection between the cartridge holder and the housing is loaded with mechanical forces. Due to the notches 17a, 17b, 18a, 18b and the way the locking element is received in the window, local stress peaks in the corners of the window 15 are avoided.

The invention claimed is:

1. A cartridge holder for a drug delivery device, a holder having a longitudinal axis, an outside surface, an inner section and comprising snap fastening connection means for fastening the cartridge holder to a housing of a drug delivery device, wherein the snap fastening connection means comprises a rectangular window located at a proximal end of the cartridge holder for receiving a locking element of the housing, where the window is a rectangular shaped through opening having four edges and connects the inner section with the outside surface,     wherein a first set of notches formed as round contours define two of corners of the window and a second set of notches formed as round contours define two other corners of the window, where the first set of notches are offset from the edges and extend in a circumferential direction with respect to the longitudinal direction and the second set of notches extend in an axial direction along the longitudinal direction, wherein the second set of notches extend less distance in the axial direction compared to a circumferential distance that the first set of notches extend.

2. The cartridge holder according to claim 1, characterized in that the first notches are arranged in such way that an intermediate section between the first notches constitutes a preferably resilient lug.

3. The cartridge holder according to claim 1, characterized in that on at least a section of an outer surface of the cartridge holder at least one axially elongated spline element, preferably integrally formed with the cartridge holder, is disposed.

4. The cartridge holder according to claim 3, characterized in that a plurality of spline elements is distributed around a periphery of at least a section of the cartridge holder in a non rotationally symmetric manner.

5. A pen-type injector, having a housing and a cartridge holder according to claim 1 for a cartridge containing a medicinal product, wherein the housing and the cartridge holder are held together by a snap-fastening connection.

6. The pen-type injector according to claim 5, characterized in that the pen-type injector is a disposable injection device.

7. The cartridge holder according to claim 1 where one of the second notches extends in a distal direction and the other second notch extends in the proximal direction.

8. The cartridge holder according to claim 1 further comprising a plurality of the rectangular windows that are irregular spaced circumferentially around the proximal end of the cartridge holder.

\* \* \* \* \*